(12) United States Patent
Ehm et al.

(10) Patent No.: US 12,306,551 B2
(45) Date of Patent: May 20, 2025

(54) PROJECTION EXPOSURE APPARATUS HAVING A DEVICE FOR DETERMINING THE CONCENTRATION OF ATOMIC HYDROGEN

(71) Applicant: Carl Zeiss SMT GmbH, Oberkochen (DE)

(72) Inventors: Dirk Ehm, Beckingen (DE); Moritz Becker, Aalen (DE)

(73) Assignee: CARL ZEISS SMT GMBH, Oberkochen (DE)

( * ) Notice: Subject to any disclaimer, the term of this patent is extended or adjusted under 35 U.S.C. 154(b) by 564 days.

(21) Appl. No.: 17/702,218

(22) Filed: Mar. 23, 2022

(65) Prior Publication Data

US 2022/0308457 A1 Sep. 29, 2022

(30) Foreign Application Priority Data

Mar. 23, 2021 (DE) ...................... 10 2021 202 802.0

(51) Int. Cl.
*G03F 7/00* (2006.01)
*G01N 33/00* (2006.01)
(52) U.S. Cl.
CPC ......... *G03F 7/7085* (2013.01); *G01N 33/005* (2013.01); *G03F 7/70308* (2013.01)
(58) Field of Classification Search
CPC ............... G03F 7/7085; G03F 7/70841; G03F 7/70916; G03F 7/70033; G03F 7/702; G03F 7/70925; G03F 7/70308; G01N 33/005; G01N 1/2205; G01N 25/18; G01N 21/211; G01N 29/022; B01D 53/007
See application file for complete search history.

(56) References Cited

U.S. PATENT DOCUMENTS 6,573,978 B1 6/2003 McGuire, Jr.
2006/0132747 A1 6/2006 Singer et al.
(Continued)

FOREIGN PATENT DOCUMENTS

DE 102008009600 A1 8/2009
DE 102017205885 A1 6/2017
DE 102017205870 A1 4/2018
(Continued)

OTHER PUBLICATIONS

Velthuis et al. "Radical Recombination Sensor Based on Dual Probe Thermopile Heat Flux Sensors", Oct. 2019.*
(Continued)

*Primary Examiner* — Peter B Kim (74) *Attorney, Agent, or Firm* — Edell, Shapiro & Finnan, LLC (57) ABSTRACT

A projection exposure apparatus (1) for semiconductor lithography has a device for determining the concentration of atomic hydrogen in a plasma (29) in the region of an optical element (25, 25.1), wherein the device includes a sensor (32, 32.1, 32.2, 32.3, 32.4), In this case, the device includes a filter element (31, 31.1,31.2, 31.3, 31.4) arranged between the region of the plasma (29) and the sensor (32, 32.1, 32.2, 32.3, 32.4), wherein the filter element (31, 31.1,31.2, 31.3, 31.4) is configured to predominantly allow the passage of atomic hydrogen from the plasma (29) to the sensor (32, 32.1, 32.2, 32.3, 32.4).

19 Claims, 4 Drawing Sheets

(56) References Cited

U.S. PATENT DOCUMENTS

2018/0074303 A1   3/2018   Schwab
2020/0272058 A1   8/2020   Bieling et al.

FOREIGN PATENT DOCUMENTS

| DE | 102017220586 A1 | 5/2019 | |
|---|---|---|---|
| EP | 1614008 B1 | 12/2009 | |
| WO | WO-2022017883 A1 * | 1/2022 | ......... G01N 33/0027 |

OTHER PUBLICATIONS

German Office Action with English translation, Application No. 10 2021 202 802.0, Sep. 22, 2021, 4 pages.

* cited by examiner

PROJECTION EXPOSURE APPARATUS HAVING A DEVICE FOR DETERMINING THE CONCENTRATION OF ATOMIC HYDROGEN

CROSS-REFERENCE TO RELATED APPLICATIONS

The present patent application claims the priority of the German patent application DE 10 2021 202 802.0, filed on Mar. 23, 2021, the content of which is fully incorporated by reference in its entirety herein.

FIELD OF THE INVENTION

The invention relates to a projection exposure apparatus for semiconductor lithography, having a device for determining the concentration of atomic hydrogen in a plasma.

BACKGROUND

Projection exposure apparatuses, in particular projection exposure apparatuses for semiconductor lithography are used for producing extremely fine structures, in particular on semiconductor components or other microstructured component parts. The operating principle of these apparatuses is based on the production of very fine structures up to the nanometre range by way of generally reducing imaging of structures on a mask by way of optical elements, using what is referred to as a reticle, on an element to be structured that is provided with photosensitive material. The minimum dimensions of the structures produced are directly dependent on the wavelength of the light used.

Recently, light sources having an emission wavelength in the range of a few nanometres, for example between 1 nm and 120 nm, in particular in the extreme ultraviolet (EUV) region of 13.5 nm, have increasingly been used. The short-wave used radiation of an EUV projection exposure apparatus is absorbed by any substances—including gases—within a few mm or cm, and so it is necessary for there to be a vacuum in an EUV projection exposure apparatus.

For technical process-related reasons, however, gases are often introduced into the vacuum, such as for example hydrogen at a partial pressure of 1 to 1000 Pa. This hydrogen serves for cleaning and for protection from contamination, in particular oxides, on optical surfaces and is predominantly in a molecular form ($H_2$). As a result of the radiation emitted by the used light source, however, a plasma arises in combination with the molecular hydrogen $H_2$ in the spatial region adjacent to an optically effective surface of the optical elements. This plasma includes atomic hydrogen H, electrons $e^-$ and ions, for example $H_3^+$, in addition to molecular hydrogen $H_2$. The term optically effective surface is intended to be understood here as meaning the region of the optical element that is impinged by used radiation during the operation of the apparatus. In addition to the cleaning effect, the atomic hydrogen H also has the tendency to bond to process residues, for example zinc or lead. This so-called hydrogen-induced contamination can in turn lead to a loss of transmission on the optical elements.

Furthermore, the atomic hydrogen also has an etching effect, and so it for example attacks the main material of the optical elements, which are generally designed in the form of mirrors. To set the ratio of cleaning on the one hand and hydrogen-induced contamination and etching effect on the other hand, it is therefore necessary to know the concentration of the atomic hydrogen in the plasma. In principle, this can be determined by various measurement methods, such as heat flux measurements or etch rates, or by spectroscopy. What is common to all measurement types is that measurement errors are caused by the ions $H_3^+$ and electrons $e^-$ additionally present in the plasma in addition to the atomic hydrogen H, and also by atomic hydrogen H with too much energy. By way of example, a heat flux measurement is only possible if no electrons or ions are incident on the corresponding heat flux sensor. In principle, this is possible on account of the short life of the electrons e- and ions $H_3^+$ in comparison with atomic hydrogen H, but has as a consequence that the EUV radiation must be switched off for a measurement so that the plasma can decay. A disadvantage thereof is that no measurement is possible during operation and the time required for the measurement cannot be used to produce structured elements, which in turn has a negative effect on the productivity of the associated projection exposure apparatus.

SUMMARY

It is an object of the present invention to provide a device which eliminates the above-described disadvantages of the prior art.

This object is achieved by a device and a method having the features of the independent claims. The dependent claims relate to advantageous developments and variants of the invention.

A projection exposure apparatus according to the invention for semiconductor lithography having a device for determining the concentration of atomic hydrogen in a plasma in the region of an optical element comprises a sensor and a filter element arranged between the region of the plasma and the sensor, wherein the filter element is configured to predominantly allow the passage of atomic hydrogen from the plasma to the sensor.

What is achieved by the filter element according to the invention is that it is not necessary to deactivate the used light source for a measurement and not necessary to await the decay of the remaining plasma constituents in order to be able to carry out a measurement. Rather, the production operation of the projection exposure apparatus can be accompanied by the measurement being carried out.

In principle, the optical element can be any element used in a projection exposure apparatus, that is to say also a collector mirror used in the illumination system or in the light source.

In particular, the filter element can comprise a channel-shaped region for the passage of the atomic hydrogen. In this case, the creation of a channel-shaped region between the region of the plasma and the sensor is advantageous in that additional surfaces are available on the channel inner side, on which the charged constituents of the plasma can recombine. Filtering of the plasma is achieved on the path to the sensor since the recombination rate of the charged constituents is typically higher than that of the atomic hydrogen, as a consequence of which the sensor is preferably reached by atomic hydrogen and not by other constituents of the plasma.

In an advantageous variant of the invention, the inner sides of the channel-shaped region are at least partly formed such that there is a low recombination probability when atomic hydrogen is incident thereon. This is particularly the case for metallic, oxidized and preferably ceramic surfaces, which have aluminium oxide for example. Particularly efficient filtering can be achieved by virtue of the ratio of length to smallest diameter of the channel-shaped region ranging between 20:1 and 4:1, preferably ranging between 8:1 and 4:1, particularly preferably being of the order of 6:1 at least in sections. Variants in which the channel-shaped region has sections which are angled to one another, each with different ratios of length to diameter, are also feasible.

In an advantageous embodiment of the invention, the channel shaped region is aligned at an angle of more than 30° with respect to the polarization direction of the used radiation incident on the optical element. What this achieves is that plasma electrons which typically move in the polarization direction of the EUV radiation cannot reach the sensor on a direct path, that is to say without contact on one of the inner faces of the filter element.

In particular, the channel-shaped region can have an angled embodiment. What the angled embodiment achieves is that there is no line of sight between the plasma and sensor, preventing direct incidence of one of the elements present in the plasma (H, $H_2$, $H_3^+$, $e^-$) on the sensor.

In particular, the channel-shaped region can be formed by the interaction of a main body of the optical element and a housing. In this way, a geometric structure already present can advantageously be used as a filter element.

When the optical element is a non-actuated mirror of the projection exposure apparatus, the described channel-shaped region can be formed in a particularly simple manner.

As a result of a device for producing an electric or magnetic field being arranged between the region of the plasma and the sensor, a filter effect or an improvement in the filter effect can be obtained—in conjunction with the channel-shaped region or else without the channel-shaped region—by the effect of the electrostatic or Lorentz force.

In advantageous variants of the invention, the sensor can be designed as a heat flux sensor; it may also comprise a carbon sample.

In particular, the sensor can comprise sacrificial material which experiences etch removal when exposed to H radicals. In this case, the sacrificial material can comprise C, Si, Zn, Sn, Pb, In, P or a mixture of the aforementioned elements; preferably, C or Si should be used.

Here, a device for determining the etch removal can advantageously be present.

By way of example, the etch removal can be determined by way of a transmission measurement, an ellipsometry measurement or a measurement of a frequency shift of a quartz microbalance (QMB) accompanying the loss of mass.

BRIEF DESCRIPTION OF THE DRAWINGS

Exemplary embodiments and variants of the invention are explained in more detail below with reference to the drawing, in which:

FIGS. 4 and 4A show a different variant of another embodiment of the invention, in which

DETAILED DESCRIPTION

Figure 1:
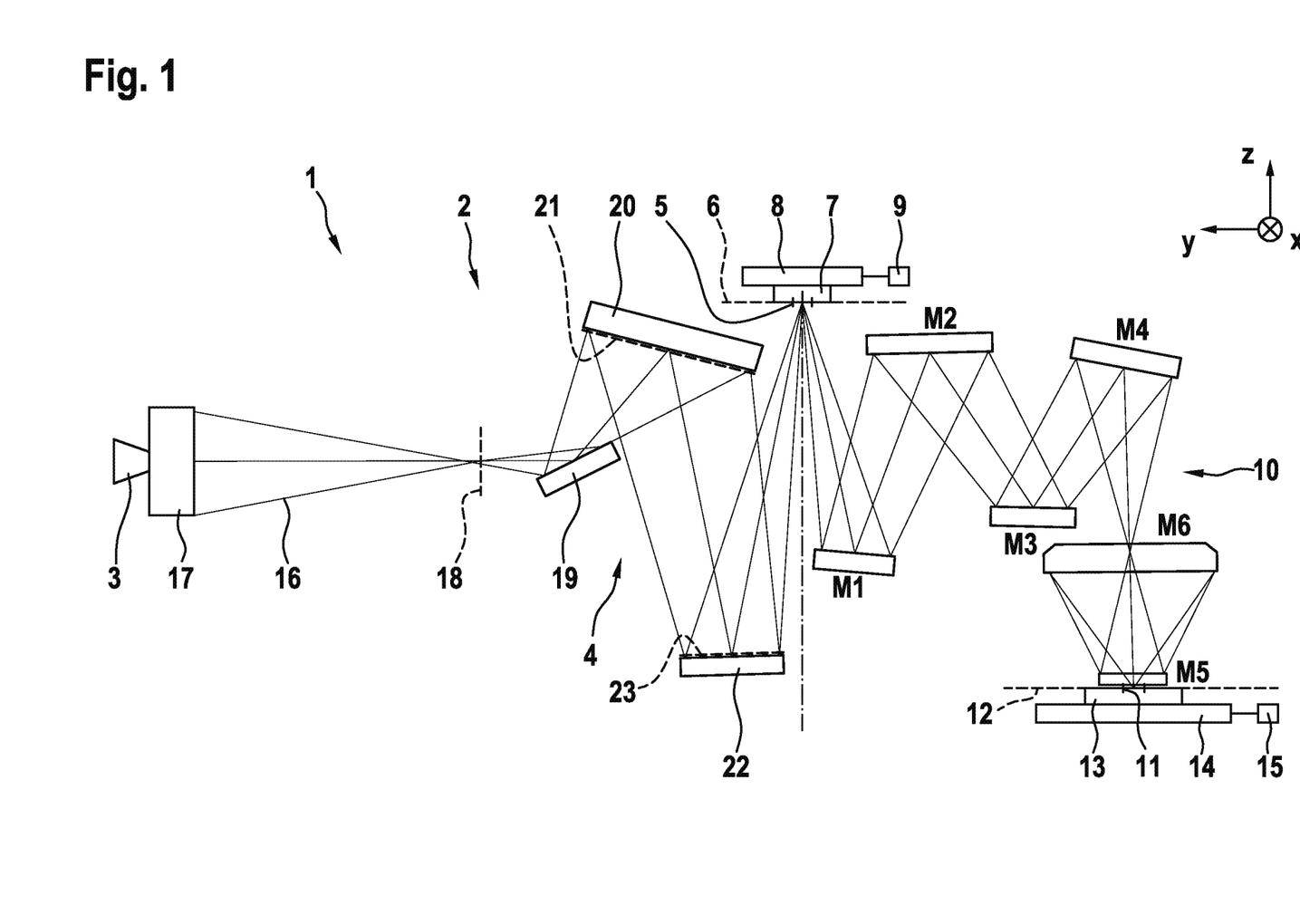
FIG. 1 schematically shows a meridional section of a projection exposure apparatus for EUV projection lithography.

With reference to FIG. 1, the essential components of a microlithographic projection exposure apparatus 1 are initially described below in exemplary fashion. The description of the basic structure of the projection exposure apparatus 1 and its components are here not understood to be limiting.

An embodiment of an illumination system 2 of the projection exposure apparatus 1 has, in addition to a radiation source 3, an illumination optical unit 4 for illuminating an object field 5 in an object plane 6. In an alternative embodiment, the light source 3 can also be provided as a separate module from the remaining illumination system. In this case, the illumination system does not comprise the light source 3.

A reticle 7 arranged in the object field 5 is exposed. The reticle 7 is held by a reticle holder 8. The reticle holder 8 is displaceable by way of a reticle displacement drive 9, in particular in a scanning direction.

A Cartesian xyz-coordinate system is shown in FIG. 1 for explanation purposes. The x-direction runs perpendicularly to the plane of the drawing into the latter. The y-direction runs horizontally and the z-direction runs vertically. The scanning direction extends along the y-direction in FIG. 1. The z-direction runs perpendicular to the object plane 6.

The projection exposure apparatus 1 comprises a projection optical unit 10. The projection optical unit 10 serves for imaging the object field 5 into an image field 11 in an image plane 12. The image plane 12 runs parallel to the object plane 6. Alternatively, an angle between the object plane 6 and the image plane 12 that differs from 0° is also possible.

A structure on the reticle 7 is imaged onto a light-sensitive layer of a wafer 13 arranged in the region of the image field 11 in the image plane 12. The wafer 13 is held by a wafer holder 14. The wafer holder 14 is displaceable by way of a wafer displacement drive 15, in particular along the y-direction. The displacement on the one hand of the reticle 7 by way of the reticle displacement drive 9 and on the other hand of the wafer 13 by way of the wafer displacement drive 15 can take place in such a way as to be synchronized with one another.

The radiation source 3 is an EUV radiation source. The radiation source 3 emits, in particular, EUV radiation 16, which is also referred to below as used radiation, illumination radiation or illumination light. In particular, the used radiation has a wavelength in the range between 5 nm and 30 nm. The radiation source 3 can be a plasma source, for example an LPP source (Laser Produced Plasma) or GDPP source (Gas Discharged Produced Plasma). It can also be a synchrotron-based radiation source. The radiation source 3 can be a free electron laser (FEL).

The illumination radiation 16 emerging from the radiation source 3 is focused by a collector 17. The collector 17 may be a collector with one or more ellipsoidal and/or hyperboloidal reflection surfaces. The illumination radiation 16 may be incident on the at least one reflection surface of the collector 17 with grazing incidence (GI), that is to say at angles of incidence of greater than 45°, or with normal incidence (NI), i.e. at angles of incidence of less than 45°. The collector 17 can be structured and/or coated, firstly, for optimizing its reflectivity for the used radiation and, secondly, for suppressing extraneous light.

Downstream of the collector 17, the illumination radiation 16 propagates through an intermediate focus in an intermediate focal plane 18. The intermediate focal plane 18 may represent a separation between a radiation source module, having the radiation source 3 and the collector 17, and the illumination optical unit 4.

The illumination optical unit 4 comprises a deflection mirror 19 and, arranged downstream thereof in the beam path, a first facet mirror 20. The deflection mirror 19 may be a plane deflection mirror or, alternatively, a mirror with a beam-influencing effect that goes beyond the purely deflecting effect. As an alternative or in addition thereto, the deflection mirror 19 can be embodied as a spectral filter separating a used light wavelength of the illumination radiation 16 from extraneous light having a wavelength that deviates therefrom. If the first facet mirror 20 is arranged in a plane of the illumination optical unit 4 that is optically conjugate to the object plane 6 as a field plane, it is also referred to as a field facet mirror. The first facet mirror 20 comprises a multiplicity of individual first facets 21, which are also referred to below as field facets. Some of these facets 21 are shown in FIG. 1 only by way of example.

The first facets 21 may be embodied as macroscopic facets, in particular as rectangular facets or as facets with an arcuate peripheral contour or a peripheral contour of part of a circle. The first facets 21 may be embodied as plane facets or alternatively as convexly or concavely curved facets.

As known for example from DE 10 2008 009 600 A1, the first facets 21 themselves may also be composed in each case of a multiplicity of individual mirrors, in particular a multiplicity of micromirrors. The first facet mirror 20 may in particular be formed as a microelectromechanical system (MEMS system). For details, reference is made to DE 10 2008 009 600 A1.

Between the collector 17 and the deflection mirror 19, the illumination radiation 16 travels horizontally, that is to say along the y-direction.

In the beam path of the illumination optical unit 4, a second facet mirror 22 is arranged downstream of the first facet mirror 20. If the second facet mirror 22 is arranged in a pupil plane of the illumination optical unit 4, it is also referred to as a pupil facet mirror. The second facet mirror 22 may also be arranged at a distance from a pupil plane of the illumination optical unit 4. In this case, the combination of the first facet mirror 20 and the second facet mirror 22 is also referred to as a specular reflector. Specular reflectors are known from US 2006/0132747 A1, EP 1 614 008 B1 and U.S. Pat. No. 6,573,978.

The second facet mirror 22 comprises a plurality of second facets 23. In the case of a pupil facet mirror, the second facets 23 are also referred to as pupil facets.

The second facets 23 can likewise be macroscopic facets, which can, for example, have a round, rectangular or hexagonal boundary, or alternatively be facets composed of micromirrors. In this regard, reference is likewise made to DE 10 2008 009 600 A1.

The second facets 23 may have planar or alternatively convexly or concavely curved reflection surfaces.

The illumination optical unit 4 consequently forms a twice-faceted system. This basic principle is also referred to as a honeycomb condenser (fly's eye integrator).

It may be advantageous to arrange the second facet mirror 22 not exactly in a plane that is optically conjugate to a pupil plane of the projection optical unit 10. In particular, the pupil facet mirror 22 can be arranged so as to be tilted relative to a pupil plane of the projection optical unit 7, as is described, for example, in DE 10 2017 220 586 A1.

The individual first facets 21 are imaged into the object field 5 with the aid of the second facet mirror 22. The second facet mirror 22 is the last beam-shaping mirror or else, in fact, the last mirror for the illumination radiation 16 in the beam path before the object field 5.

In a further embodiment of the illumination optical unit 4 that is not shown, a transmission optical unit contributing in particular to the imaging of the first facets 21 into the object field 5 may be arranged in the beam path between the second facet mirror 22 and the object field 5. The transmission optical unit may have exactly one mirror or else alternatively two or more mirrors, which are arranged one behind the other in the beam path of the illumination optical unit 4. The transmission optical unit may in particular comprise one or two normal-incidence mirrors (NI mirrors) and/or one or two grazing-incidence mirrors (GI mirrors).

In the embodiment shown in FIG. 1, the illumination optical unit 4 has exactly three mirrors downstream of the collector 17, specifically the deflection mirror 19, the field facet mirror 20 and the pupil facet mirror 22.

The deflection mirror 19 can also be dispensed with in a further embodiment of the illumination optical unit 4, and so the illumination optical unit 4 can then have exactly two mirrors downstream of the collector 17, specifically the first facet mirror 20 and the second facet mirror 22.

As a rule, the imaging of the first facets 21 into the object plane 6 via the second facets 23 or using the second facets 23 and a transmission optical unit is only approximate imaging.

The projection optical unit 10 comprises a plurality of mirrors Mi, which are consecutively numbered in accordance with their arrangement in the beam path of the projection exposure apparatus 1.

In the example illustrated in FIG. 1, the projection optical unit 10 comprises six mirrors M1 to M6. Alternatives with four, eight, ten, twelve or any other number of mirrors Mi are similarly possible. The penultimate mirror M5 and the last mirror M6 each have a through opening for the illumination radiation 16. The projection optical unit 10 is a double-obscured optical unit. The projection optical unit 10 has an image-side numerical aperture which is greater than 0.3 and which can also be greater than 0.6 and can, for example, be 0.7 or 0.75.

Reflection surfaces of the mirrors Mi can be embodied as free-form surfaces without an axis of rotational symmetry. Alternatively, the reflection surfaces of the mirrors Mi may be designed as aspherical surfaces with exactly one axis of rotational symmetry of the reflection surface form. Just like the mirrors of the illumination optical unit 4, the mirrors Mi may have highly reflective coatings for the illumination radiation 16. These coatings may be designed as multilayer coatings, in particular with alternating layers of molybdenum and silicon.

The projection optical unit 10 has a large object image offset in the y-direction between a y-coordinate of a centre of the object field 5 and a y-coordinate of the centre of the image field 11. In the y-direction, this object-image offset can be approximately the same size as a z-distance between the object plane 6 and the image plane 12.

In particular, the projection optical unit 10 may have an anamorphic form. In particular, it has different imaging scales $\beta x$, $\beta y$ in the x- and y-directions. The two imaging scales $\beta x$, $\beta y$ of the projection optical unit 10 preferably lie at $(\beta x, \beta y)=(+/-0.25, /+-0.125)$. A positive imaging scale $\beta$ means imaging without an image reversal. A negative sign for the imaging scale $\beta$ means imaging with an image reversal.

The projection optical unit 10 consequently leads to a reduction in size with a ratio of 4:1 in the x-direction, that is to say in a direction perpendicular to the scanning direction.

The projection optical unit 10 leads to a reduction in size of 8:1 in the y-direction, that is to say in the scanning direction.

Other imaging scales are similarly possible. Imaging scales with the same sign and the same absolute value in the x-direction and y-direction are also possible, for example with absolute values of 0.125 or of 0.25.

The number of intermediate image planes in the x-direction and in the y-direction in the beam path between the object field 5 and the image field 11 may be the same or, depending on the embodiment of the projection optical unit 10, may differ. Examples of projection optical units with different numbers of such intermediate images in the x- and y-directions are known from US 2018/0074303 A1.

In each case one of the pupil facets 23 is assigned to exactly one of the field facets 21 for forming in each case an illumination channel for illuminating the object field 5. In particular, this can yield illumination according to the Köhler principle. The far field is decomposed into a multiplicity of object fields 5 with the aid of the field facets 21. The field facets 21 produce a plurality of images of the intermediate focus on the pupil facets 23 respectively assigned thereto.

The field facets 21 are imaged, in each case by way of an assigned pupil facet 23, onto the reticle 7 in a manner such that they are superposed on one another for the purposes of illuminating the object field 5. The illumination of the object field 5 is in particular as homogeneous as possible. It preferably has a uniformity error of less than 2%. The field uniformity can be achieved by way of the superposition of different illumination channels.

The illumination of the entrance pupil of the projection optical unit 10 can be defined geometrically by way of an arrangement of the pupil facets. The intensity distribution in the entrance pupil of the projection optical unit 10 can be set by selecting the illumination channels, in particular the subset of the pupil facets which guide light. This intensity distribution is also referred to as illumination setting.

A likewise preferred pupil uniformity in the region of defined illuminated sections of an illumination pupil of the illumination optical unit 4 can be achieved by a redistribution of the illumination channels.

Further aspects and details of the illumination of the object field 5 and in particular of the entrance pupil of the projection optical unit 10 are described below.

In particular, the projection optical unit 10 may have a homocentric entrance pupil. The latter may be accessible. It may also be inaccessible.

The entrance pupil of the projection optical unit 10 cannot be exactly illuminated using the pupil facet mirror 22 on a regular basis. In the case of imaging the projection optical unit 10 in which the centre of the pupil facet mirror 22 is telecentrically imaged onto the wafer 13, the aperture rays often do not intersect at a single point. However, it is possible to find an area in which the distance of the aperture rays determined in pairs becomes minimal. This area represents the entrance pupil or an area in real space that is conjugate thereto. In particular, this area has a finite curvature.

It may be that the projection optical unit 10 has different positions of the entrance pupil for the tangential beam path and for the sagittal beam path. In this case, an imaging element, in particular an optical component part of the transmission optical unit, should be provided between the second facet mirror 22 and the reticle 7. With the aid of this optical element, the different position of the tangential entrance pupil and the sagittal entrance pupil can be taken into account.

In the arrangement of the components of the illumination optical unit 4 illustrated in FIG. 1, the pupil facet mirror 22 is arranged in an area conjugate to the entrance pupil of the projection optical unit 10. The field facet mirror 20 is arranged in tilted fashion with respect to the object plane 6. The first facet mirror 20 is arranged in tilted fashion with respect to an arrangement plane defined by the deflection mirror 19.

The first facet mirror 20 is arranged so as to be tilted in relation to an arrangement plane defined by the second facet mirror 22.

Figure 2:
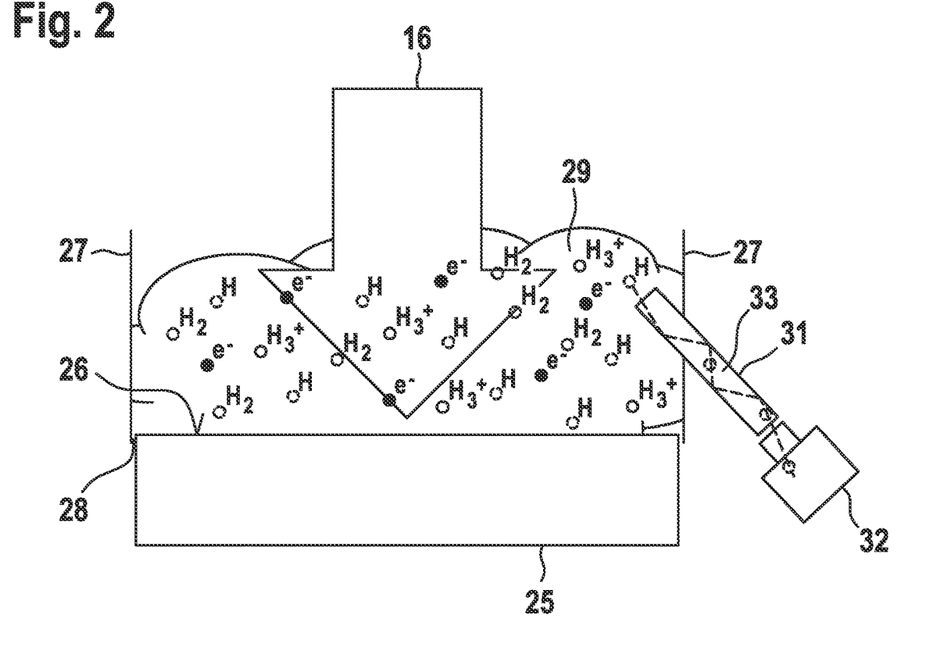
FIG. 2 shows a first embodiment of the invention.

FIG. 2 shows a first embodiment of the invention and illustrates a mirror 25, which corresponds for example to one of the mirrors M1 to M6 or 19, 20, 22 or to a collector mirror of the projection exposure apparatus 1 that was described in FIG. 1. The mirror 25 is partly enclosed by a housing 27, with a small gap 28 forming between the housing 27 and the mirror 25. This gap prevents a transmission of mechanical excitation and permits a gas exchange between the region surrounded by the housing 27 and the surroundings.

The mirror 25 comprises a mirror surface 26, which is impinged by the EUV radiation 16 used for imaging purposes. As a result of the action of the EUV radiation 16 on the molecular hydrogen $H_2$ present in the vacuum of the projection exposure apparatus 1, what is known as a plasma 29 forms above the mirror surface 26. In this context, a plasma within the meaning of the present invention should be understood to mean a mixture of molecular hydrogen $H_2$, $H_3^+$ ions and other H-containing ions, electrons $e^-$ and atomic hydrogen H. Furthermore, a sensor 32 comprising a filter element 31 is arranged outside of the housing 27, the filter element comprising a channel-shaped region 33, having a tubular embodiment in the shown example and, in particular, being able to have a rectangular or round cross section.

Furthermore, the inner faces of the filter element 31 are designed such that there is a low recombination probability when atomic hydrogen H is incident thereon. This is the case for metallic, oxidized and preferably ceramic surfaces, which have aluminium oxide for example. The aspect ratio of the filter element 31 of length to smallest diameter ranges between 4:1 and 8:1, is preferably 6:1, wherein the smallest height should be no more than 4 mm. With one end, the filter element 31 is oriented in the direction of the sensor 32, with the other end penetrating the housing 27 such that it protrudes into the plasma 29 above the mirror surface 26.

The filter element 31 is configured to only supply the sensor 32 with atomic hydrogen H. Therefore, as shown in the figure, it is preferably arranged at a flat angle in relation to the direction of the EUV radiation 16, which is indicated by an arrow. This prevents electrons $e^-$ from the plasma 29, which typically move perpendicular to the beam direction of the EUV radiation 16 (indicated in exemplary fashion in FIG. 2 for an electron $e^-$ with an arrow not labelled separately), from reaching the sensor 32 not on a direct path, that is to say without contact on one of the inner surfaces of the filter element 32.

The electrons e and the ions $H_3^+$, that is to say the charged particles of the plasma 29, are already eliminated by contact with the filter element 31, and so only the atomic hydrogen H reaches the sensor 32. The recombination probability of the atomic hydrogen H ranges between a few thousandths to 20% as a result of the housing 27 which is frequently oxidized, for example after venting, as a result of which the atomic hydrogen H can advance to the sensor 32 even in the case of a plurality of contacts with the housing 27 and the filter element 31.

To determine the concentration of the atomic hydrogen H above the mirror surface 26, it is necessary to simulate the concentration of ions $H_3^+$, atomic hydrogen H and electrons $e^-$ in the plasma and the reduction of the atomic hydrogen H on the path from the plasma to the sensor 32 depending on the time-varying surface quality in the filter element 31. The time variation has to be considered because surfaces, in particular metal, may be oxidized after venting, leading to a low recombination probability. However, the surfaces are successively reduced by the atomic hydrogen and the ionic plasma species penetrating into the entrance region of the filter element 31, and so the recombination probability increases. The simulations are validated by experiments under similar or identical geometric and ambient conditions. In the exemplary embodiment shown, the sensor 32 is designed as heat flux sensor which can directly ascertain the concentration of the atomic hydrogen H. Alternatively, the concentration of the atomic hydrogen can also be detected, for example, by way of a carbon etching rate. The arrangement of the carbon sample is identical to that of the heat flux sensor since ions or electrons on the sensor would likewise falsify the result. In this case, the etching rate can be determined by a transmission measurement, a vibration quartz balance, an ellipsometry measurement or an ex-situ analysis.

Figure 3:
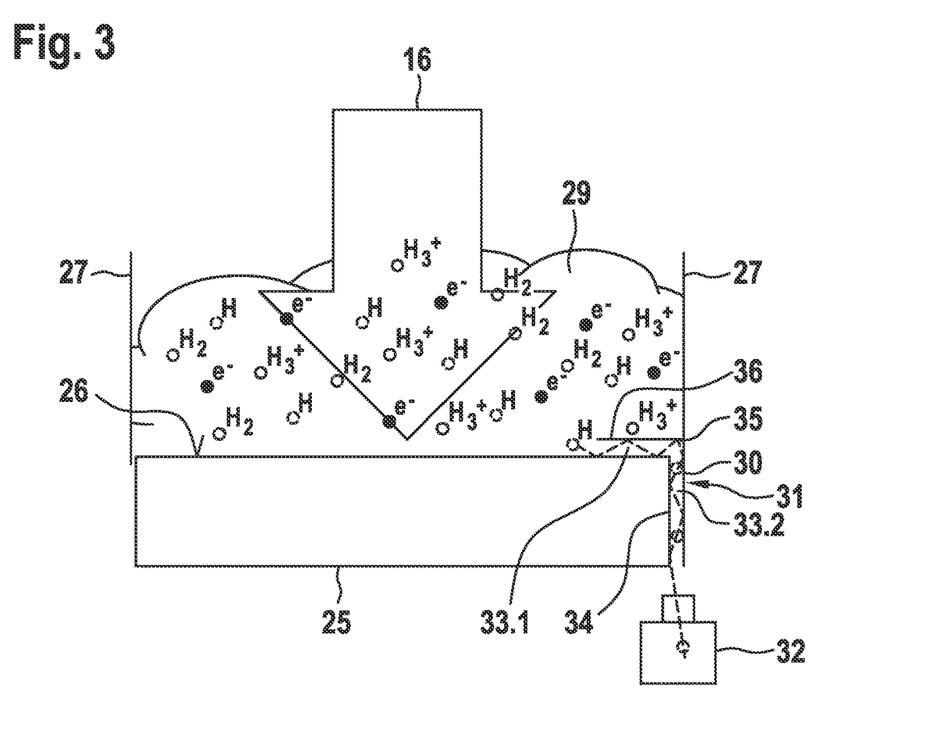
FIG. 3 shows a further embodiment of the invention.

FIG. 3 shows a further embodiment of the invention, in which a mirror 25 surrounded by a housing 27 is likewise illustrated. In contrast to the embodiment described in FIG. 2, the filter element 31 is integrated in the housing 27. To avoid a direct incidence of charged particles (e⁻, $H_3^+$) and of atomic hydrogen H with too much energy, which would lead to a measurement error in the utilized heat flux sensor 32, the filter element 31 is formed with a bend 35. In the shown exemplary embodiment, the bend 35 is 90 degrees, with the bend 35 only having to be so large that there is no line of sight between the plasma 29 and sensor 32, preventing direct incidence of one of the elements present in the plasma 29 (H, $H_2$, $H_3^+$, e⁻) on the sensor 32. The filter element 31 has a first portion 33.1 formed as a channel, which runs parallel to the mirror surface 26 of the mirror 25 and which is formed by the mirror surface 26 and a channel element 36 connected to the housing 27. This first portion 33.1 is connected via the bend 35 to a second portion 33.2 of the filter element 31, which second portion is formed by the side face 34 of the mirror and an extension 30 of the housing 27 and which runs perpendicular to the first portion 33.1 between the mirror 25 and the housing 27. The sensor 32 is arranged at the end of the second portion 33.2. In principle, the filter element can also be formed as a magnetic or electric field, which deflects the charged particles $H_3^+$, e" such that these do not strike the sensor 32. However, in the case of too much energy, that is to say too much speed, the uncharged atomic hydrogen H directly striking the sensor 32 may lead to disturbances in the measurement.

Different variants of possible embodiments of the invention will be explained below on the basis of FIG. 4 and FIG. 4A. In the example shown in FIG. 4, a mirror 25.1 is also located within a housing 27.1 and is impinged by illumination radiation 16. Furthermore, individual electrons and H3+ ions are represented in the figures with their movement directions and speeds, which are indicated by arrows. In a first variant of the invention a filter element 31.1, which is essentially formed as a straight channel and which comprises a sensor 32.1, is provided with a region through which a magnetic field passes. In the figure, this is indicated by the indicated course of a current-carrying conductor, not labelled separately in the figure, and the corresponding symbol for the B-field. As a result of the presence of the B-field, charged particles which enter into the filter element 31.1 are deflected toward the wall of the filter element, as elucidated on the basis of the detailed illustration in FIG. 4A.

A complementary or alternative filter element 31.2 is illustrated below the filter element 31.1 in FIG. 4. In this case, the filter effect is improved by virtue of the filter element 31.2 with its sensor 32.2 being arranged at a comparatively flat angle with respect to the propagation direction of the incident or reflected illumination radiation 16. The filter element 31.2, too, is oriented in the direction of the sensor 32.2 with one end, with the other end not penetrating the housing 27.1 but sampling the flux of atomic hydrogen H on a surface element of the housing 27.1. What this achieves is that the sensor 32.2 of the filter element 31.2 is reached by as few photoelectrons as possible, the latter arising by the interaction of the illumination radiation 16 with the plasma or the gas located in the region of the optical element 25.1. For illustration purposes, FIG. 5 shows, without any detailed labelling of the individual elements shown in the figure, a twin lobe-shaped directional distribution of the photoelectrons in relation to the propagation direction of electromagnetic radiation (linearly polarized electric radiation in the example shown). Something analogous applies to a circular polarization.

Figure 4:
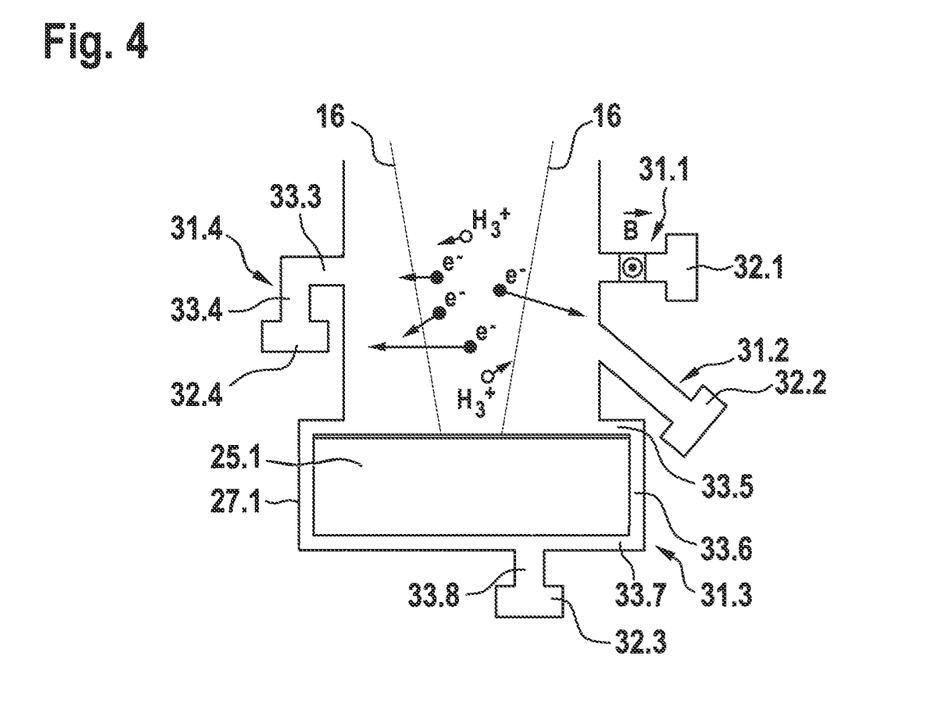
Figure 4A:
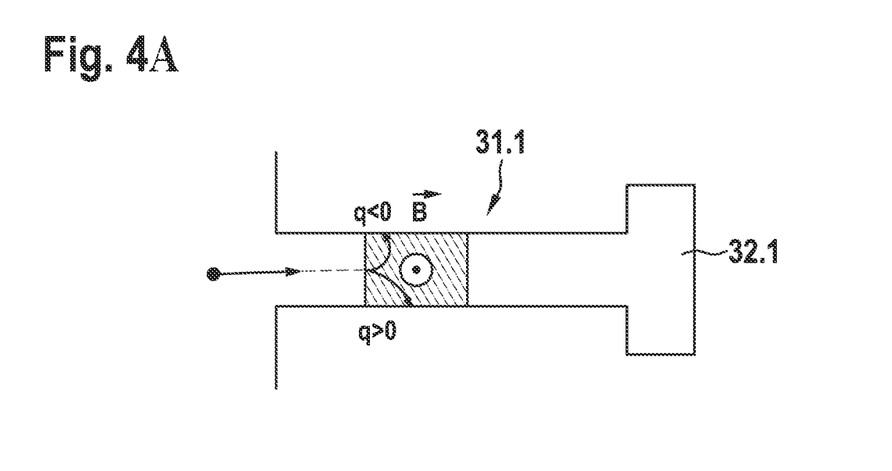
FIG. 4A shows a portion of FIG. 4 in enlarged detail.
Figure 5:
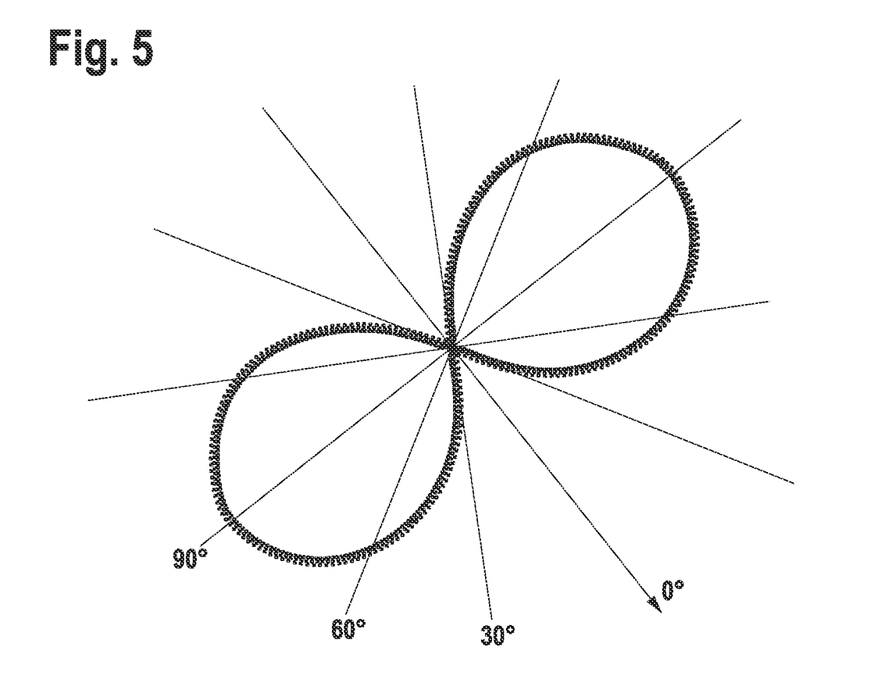
FIG. 5 shows a directional distribution of photoelectrons in relation to the propagation direction of electromagnetic radiation.

A variant of an angled embodiment of the filter element 31.3 including the housing 27.1 is likewise illustrated in FIG. 4. In the process, individual portions 33.5 to 33.8, which are arranged at an angle to one another, arise from the geometry of the housing 27.1 and of the optical element 25.1. This likewise results in an effective filtration of unwanted charged particles, and hence an effective protection for the sensor 32.3.

A slightly simplified embodiment of an angled filter element 31.4, with the two portions 33.4 and 33.3, is shown in the left region of the housing 27.1 in FIG. 4, the portions likewise being arranged at an angle and consequently likewise shielding the sensor 32.4 from an impingement by unwanted charged particles.

LIST OF REFERENCE SIGNS

1 Projection exposure apparatus
2 Illumination system
3 Radiation source
4 Illumination optical unit
5 Object field
6 Object plane
7 Reticle
8 Reticle holder
9 Reticle displacement drive
10 Projection optical unit
11 Image field
12 Image plane
13 Wafers
14 Wafer holder
15 Wafer displacement drive
16 EUV radiation
17 Collector
18 Intermediate focal plane
19 Deflection mirror
20 Facet mirror
21 Facets
22 Facet mirror
23 Facets
25, 25.1 Mirror
26 Mirror surface
27, 27.1 Housing
28 Gap
29 Plasma
30 Housing extension 31, 31.1, 31.2, 31.3, Filter element
31.4
32, 32.1, 32.2, 32.3, Sensor
32.4
33, 33.1-33.8 Channel-shaped region, portions
34 Side face of a mirror
35 Bend
36 Channel element
e⁻ Electron
H Atomic hydrogen
H$_2$ Molecular hydrogen
H$_3^+$ Hydrogen ion

What is claimed is:

1. Projection exposure apparatus for semiconductor lithography, comprising a device for determining concentration of atomic hydrogen in a plasma in a region of an optical element, wherein the device comprises:
    a sensor, and
    a filter element arranged between the region of the plasma and the sensor, wherein the filter element is configured to predominantly allow passage of atomic hydrogen from the plasma to the sensor, and
wherein the filter element comprises a channel-shaped region for the passage of the atomic hydrogen.

2. Projection exposure apparatus according to claim 1, wherein inner sides of the channel-shaped region are at least partly formed such that there is a low recombination probability when atomic hydrogen is incident thereon.

3. Projection exposure apparatus according to claim 1, wherein a ratio of length to smallest diameter of the channel-shaped region ranges between 20:1 and 4:1 at least in sections of the region.

4. Projection exposure apparatus according to claim 3, wherein the ratio of the length to the smallest diameter of the channel-shaped region ranges between 8:1 and 4:1 at least in the sections of the region.

5. Projection exposure apparatus according to claim 4, wherein the ratio of the length to the smallest diameter of the channel-shaped region is of the order of 6:1 at least in the sections of the region.

6. Projection exposure apparatus according to claim 1, wherein the channel shaped region is aligned at an angle of >30° with respect to a polarization direction of used radiation incident on the optical element.

7. Projection exposure apparatus according to claim 1, wherein the channel-shaped region has an angled configuration.

8. Projection exposure apparatus according to claim 7, wherein the channel-shaped region is formed by interaction of a main body of the optical element and a housing.

9. Projection exposure apparatus according to claim 1, wherein the optical element is a non-actuated mirror of the projection exposure apparatus.

10. Projection exposure apparatus according to claim 1, wherein a device for producing an electric or magnetic field is arranged between the region of the plasma and the sensor.

11. Projection exposure apparatus according to claim 1, wherein the sensor is a heat flux sensor.

12. Projection exposure apparatus for semiconductor lithography, comprising a device for determining concentration of atomic hydrogen in a plasma in a region of an optical element, wherein the device comprises:
    a sensor, and
    a filter element arranged between the region of the plasma and the sensor, wherein the filter element is configured to predominantly allow passage of atomic hydrogen from the plasma to the sensor, and
wherein the sensor comprises a sacrificial material which experiences etch removal when exposed to H radicals.

13. Projection exposure apparatus according to claim 12, wherein the sacrificial material contains one or more of the substances Zn, Sn, Pb, In, P, C, or Si.

14. Projection exposure apparatus according to claim 13, wherein the sacrificial material contains C or Si.

15. Projection exposure apparatus according to claim 12, further comprising a device for determining the etch removal.

16. Projection exposure apparatus according to claim 15, wherein the etch removal determining device is configured to carry out a transmission measurement, an ellipsometry measurement or a measurement of a frequency shift of a quartz microbalance.

17. Projection exposure apparatus according to claim 12, wherein the optical element is a non-actuated mirror of the projection exposure apparatus.

18. Projection exposure apparatus according to claim 12, wherein a device for producing an electric or magnetic field is arranged between the region of the plasma and the sensor.

19. Projection exposure apparatus according to claim 12, wherein the sensor is a heat flux sensor.

* * * * *

UNITED STATES PATENT AND TRADEMARK OFFICE
CERTIFICATE OF CORRECTION

| | | |
|---|---|---|
| PATENT NO. | : 12,306,551 B2 | Page 1 of 1 |
| APPLICATION NO. | : 17/702218 | |
| DATED | : May 20, 2025 | |
| INVENTOR(S) | : Ehm et al. | |

It is certified that error appears in the above-identified patent and that said Letters Patent is hereby corrected as shown below:

On the Title Page

Column 2, under "(57) ABSTRACT", Line 6, delete "31.1,31.2," and insert -- 31.1, 31.2, --.

Column 2, under "(57) ABSTRACT", Line 9, delete "31.1,31.2," and insert -- 31.1, 31.2, --.

In the Specification

Column 2, Line 10, delete "e-" and insert -- $e^-$ --.

Column 3, Line 6, delete "channel shaped" and insert -- channel-shaped --.

Column 8, Line 54, delete "e" and insert -- $e^-$ --.

Column 9, Line 46, delete "e′″" and insert -- $e^-$ --.

Column 9, Line 55, delete "H3+" and insert -- $H_3^+$ --.

Column 11, Line 1, delete "31.1,31.2," and insert -- 31.1, 31.2, --.

Signed and Sealed this
Twenty-fifth Day of November, 2025

John A. Squires
*Director of the United States Patent and Trademark Office*